(12) United States Patent
Schmidt et al.

(10) Patent No.: US 7,257,243 B2
(45) Date of Patent: Aug. 14, 2007

(54) METHOD FOR ANALYZING A BIOLOGICAL SAMPLE

(75) Inventors: Robert Schmidt, Nuernberg (DE); Thomas Wittenberg, Erlangen (DE); Heinz Gerhaeuser, Waischenfeld (DE); Klaus Spinnler, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 605 days.

(21) Appl. No.: 10/478,482

(22) PCT Filed: May 14, 2002

(86) PCT No.: PCT/EP02/05316

§ 371 (c)(1),
(2), (4) Date: Jun. 8, 2004

(87) PCT Pub. No.: WO02/095394

PCT Pub. Date: Nov. 28, 2002

(65) Prior Publication Data

US 2004/0235180 A1   Nov. 25, 2004

(30) Foreign Application Priority Data

May 18, 2001 (DE) ............................... 101 24 340

(51) Int. Cl.
*G06K 9/00* (2006.01)
(52) U.S. Cl. ........................................ 382/128; 435/63
(58) Field of Classification Search ................ 382/128, 382/129, 130, 131, 132, 133, 134; 600/109, 600/160, 476; 435/6, 21, 23, 30, 63, 287.3, 435/287.6, 287.9, 459; 436/31, 46, 47, 52, 436/63, 74, 158, 174, 177, 181, 519
See application file for complete search history.

(56) References Cited

U.S. PATENT DOCUMENTS 5,162,990 A   11/1992   Odeyale et al.

(Continued)

FOREIGN PATENT DOCUMENTS

DE   19538004 A1   2/1996

(Continued)

OTHER PUBLICATIONS

Olinski, Ryszard, et al; *DNA base modifications in chromatin of human cancerous tissues*: Chemical Science and Tech Lab, National institute of Standards and Tech, Gaithersburg, MD 20899, USA; vol. 309, No. 2, 193-198; 1992 Federation of European Biochemical Societies 00145793/93—FEBS 1503; Sep. 1992.

(Continued)

*Primary Examiner*—Samir Ahmed
*Assistant Examiner*—Abolfazl Tabatabai
(74) *Attorney, Agent, or Firm*—Michael A. Glenn; Glenn Patent Group

(57) ABSTRACT

A method for the analysis of a biological sample for determining a change thereof relative to a healthy biological sample includes creating a first image of the biological sample at a first acquisition modality and creating a second image of the biological samples at a second acquisition modality. The first image is classified on the basis of a first pre-determined parameter, and the second image is classified on the basis of a second pre-determined parameter, the first image being classified independently of the second image. Then, depending on the classification results, it is determined if the biological sample comprises a change relative to a healthy biological sample.

7 Claims, 3 Drawing Sheets

U.S. PATENT DOCUMENTS

| | | | |
|---|---|---|---|
| 5,252,487 A * | 10/1993 | Bacus et al. | 436/63 |
| 5,381,224 A | 1/1995 | Dixon et al. | |
| 5,733,721 A * | 3/1998 | Hemstreet et al. | 435/6 |
| 5,755,954 A | 5/1998 | Ludwig et al. | |
| 5,978,497 A | 11/1999 | Lee et al. | |
| 5,986,271 A | 11/1999 | Lazarev et al. | |
| 5,999,844 A * | 12/1999 | Gombrich et al. | 600/476 |
| 6,005,256 A | 12/1999 | McGlynn et al. | |
| 6,081,740 A * | 6/2000 | Gombrich et al. | 600/424 |
| 6,091,842 A | 7/2000 | Domanik et al. | |
| 6,143,512 A | 11/2000 | Markovic et al. | |
| 6,246,785 B1 * | 6/2001 | Molnar et al. | 382/133 |

FOREIGN PATENT DOCUMENTS

| | | |
|---|---|---|
| DE | 19612465 A1 | 10/1997 |
| DE | 19747415 A1 | 5/1998 |
| DE | 19834718 A1 | 2/2000 |
| EP | 0 317 139 A2 | 5/1989 |
| EP | 0 647 844 A2 | 4/1995 |
| GB | 2 116 712 A | 9/1983 |
| JP | 10-185911 | 7/1998 |
| WO | WO 90/10276 | 9/1990 |
| WO | WO 97/13135 | 4/1997 |
| WO | WO 97/41416 | 11/1997 |
| WO | WO 99/01749 | 1/1999 |
| WO | WO 99/53832 | 10/1999 |

OTHER PUBLICATIONS

Olinski, Ryszard, et al; *DNA base modifications and antioxidant enzyme activities in human benign prostatic hyperplasia*; Free Radical Biology & Medicine, vol. 18, No. 4, pp. 807-813, 1995.

Musarrat, J, et al; Prognostic and Aetiological Relevance of 8-Hydroxyguanosine in Human Breast Carcinogenesis; European Journal of Cancer, vol. 32A, No. 7, pp. 1209-1214, 1996.

Forsmo, Siri, et al.; Treatment of pre-invasive conditions during opportunistic screening and its effectiveness on cervical cancer incidence in one Norwegian county; Int. J. Cancer: 71, 4-8 (1997).

Matsui, Akira, et al.; Increased formation of oxidative DNA damage . . . ; Cancer Letters 151 (2000) 87-95; www.elsevier.com/locate/canlet.

Reid, Thomas M., et al.; Tandem double CC→TT mutations are produced by reactive oxygen species; Proc. Natl. Acad. Sci. USA; vol. 90, pp. 3904-3907, May 1993.

Moriya, Masaaki; Single-stranded shuttle phagemid for mutagenesis studies in mammalian cells . . . ; Proc. Natl. Acad. Sci. USA; vol. 90, pp. 1122-1126, Feb. 1993.

Tucker, Mitchell S., et al.; A novel signature mutation for oxidative damage resembles a mutational pattern found commonly in human cancers; Cancer Research 59, pp. 1937-1839, Apr. 15, 1999.

Jaruga, Pawel, et al.; Oxidative DNA base damage and antioxidant enzyme activities in human lung cancer; FEBS Letters 341, 99 59-64; FEBS 13752; 1994.

Senturker, Sema et al; Oxidative DNA base damage and antioxidant enzyme levels in childhood acute lymphoblastic leukemia; FEBS letters 416, pp. 286-290; FEBS 19374; 1997.

Driscoll, Kevin E., et al.; Characterizing mutagenesis in the hprt gene of rat alveolar epithelial cells; Experimental Lung Research, 21:941-956, 1995.

Nehls, Peter, et al.; Formation and Persistence of 8-oxoguanine in rat lung cells as an important determinant for tumor formation following particle exposure; Environmental Health Perspectives; vol. 105, Supplement 5; Sep. 1997.

Du, Ming-Qing, et al.; Induction of activating mutations in the human c-Ha-ras-1 proto-oncogene by oxygen free radicals; Molecular Carcinogenesis 11:170-175; 1994.

* cited by examiner

METHOD FOR ANALYZING A BIOLOGICAL SAMPLE

BACKGOUND OF THE INVENTION

1. Field of the Invention

The present invention relates to a method for the analysis of a biological sample, and in particular to a method for the analysis of a tissue sample, to recognize benign or malign tissue changes in the course of the early detection and avoidance of cancer.

2. Description of the Related Art

Every year, about 6.6 million people die of cancer worldwide. In the industrialized countries, this disease is the second most frequent cause of death. Despite great financial and scientific efforts, it has not been possible to this day, to achieve a decisive breakthrough in the successful treatment of tumor diseases. From today's point of view, a noticeable reduction of the cancer incidences and mortality is only possible by innovative solutions in the area of the early detection, prognosis, and prevention of cancer.

An effective means for the early detection and avoidance of cancer is regular screening tests. By means of the cancer screening, existing tumor cells, but also still benign tissue changes, so-called dysplasia, may be evidenced. In some cases these develop further into tumors, but mostly they recede again or remain unchanged. Secured progression assessment of the tissue changes is not possible with the diagnostic methods currently applied.

The cancer screening tests are largely based on the cytological and histological analysis of tissue samples under the microscope. The interpretation of the microscopic images requires maximum competence in the art and a lot of routine. The methods of digital image processing and pattern recognition sometimes offer brilliant advantages in the classification of highly complex and sometimes also very rare images of results for the application, because they are neutral and independent of the subjective sensitivities of the viewer. Up to now, however, the required classification security has not been able to be achieved with automatic methods of the cell analysis based on gray-scale images. Especially for the screening test of the cervical carcinoma by means of a gynecological smear (a swab of the cervix) as well as for the evaluation of bronchial secretion samples, automated methods have been developed that, however, can recognize existing tumor cells only with very limited sensitivity or specificity.

By means of the method after Papanicolaou (PAP test; cytological staining method for the identification of pre-malign and malign cells in smears) it has been possible to reduce the incidence for cervical tumors in the western countries and in Japan by about 70%. Yet this test has significant deficiencies that consist in the rate of indistinct results lying at 5 to 10% and the rate of wrongly negative results lying at 5 to 50%.

In the last few years, therefore, a series of new methods has been developed, that have replaced the above-described PAP test.

One method uses an automated thin layer cell preparation technique with which dysplastic cells may be significantly better identified at the presence of only very small amounts of conspicuous cell material. This method has been approved by the American FDA (Food and Drug Association) as replacement for the conventional PAP test in 1996, and is said to improve the discovery of dysplasia by 65%, according to results of clinical studies.

Furthermore, a computer-aided image analysis method is known that is mainly employed in large cytological laboratories already today. In contrast to the PAP test in which the microscopic assessment of the swabs is done manually, this method enables an objective assessment of cellular swabs. Clinical studies in the US have shown that these automated methods lead to a reduction of the wrongly-negative results. The test just described has been approved in the US as routine diagnostics for cervical cancer screening since 1998.

The developments of the PAP test just described are suitable for at least partly eliminating the quality disadvantages of the conventional methods. But they are, just like the PAP test itself, not capable of making a reliable progression assessment of dysplasia. Repetitive and additional examinations for diagnostic clarification and for checking the dysplasia still remain necessary even with the employment of improved sample preparation and automated analysis. The conventional image analysis methods employed herewith offer two significant advantages in the classification of highly complex and rare images of results over the manual cell analysis, but with these technologies the required classification security cannot be achieved. The methods are only capable of recognizing existing tumor cells and dysplasia with very limited sensitivity and specificity (smaller than 70%).

In 1996, a DNA test for the evidencing of human papilloma viruses for the cervical cancer prevention has been introduced. The series of examinations has shown that there is a close link between the infection with human papilloma viruses (HPV) and the development of cervical lesions and cancer. HPV can be evidenced in about 99% of all invasive cervical carcinoma and in more than 90% of the higher-degree preliminary stages. The HPV typification is recognized in the western industrialized countries as the additional diagnostic examination with women with small and medium dysplasia. The problem of the HPV test for the cervical cancer prevention, however, lies in its high rate of wrongly positive results. Up to 80% of all women are infected with HPV during their lives, but only about 2 to 4% of all women actually have dysplasia, and only about 1 to 2% of these women fall sick with a cervical carcinoma.

Furthermore, a method for the recognition of bladder cancer is known in the prior art, which is based on the NMP technology (nuclear matrix protein technology). NMPs are present in the nuclei of the epithelial tissue, and have significantly increased values in bladder cancer patients, which may be evidenced in the urine by specific antibodies. Results from clinical studies show that the NMP technology evidences cervical dysplasia and tumors with a significantly higher sensitivity than the conventional PAP test.

Another method for cervical cancer prevention is the identification of specific protein markers that are overexpressed in dysplastic cells and tumor cells. Results from clinical studies relating to this method are not known.

As well as the developments of the PAP test, also the HPV typification and protein markers may significantly contribute to the improvement of quality in cervix screening cytology. None of these in-vitro diagnosis methods, however, is capable of making an objective progression statement on the development of a cell in a tumor. Additional and repetitive examinations as well as surgery taking place for safety reasons in persisting or progressive lesions cannot be prevented thereby.

In EP 0 647 844 A, a method for interactive automatic cytology is described, in which an automated system and an operator make the diagnosis in parallel, and the system diagnosis is compared with the operator diagnosis in the final step. This method has the disadvantage that here diagnosis also has to be made by an operator. In U.S. Pat. Nos. 5,7557,954 and 5,978,497, methods for automatic segmenting of an image representing a biological sample are described in greater detail, with individual objects being classified on the basis of predetermined features.

In DE 19747415 A1, a method is described to simplify analysis of a biological sample by a cytologist by determining diagnostically significant material from a sample and determining a "path" through the sample so that the viewer only has to take a look at the relevant samples.

Apart from the above-described publications in connection with the examination of cells, digital image processing systems are also known in the prior art, which are described in DE 19834718 A1, DE 19612465 A1 and DE 19538004 A1. These patents refer to general image detection and classification systems, which do not, however, guarantee sufficient classification security for the examination of biological samples for possible benign or malign changes.

SUMMARY OF THE INVENTION

Starting from the above-described prior art, it is the object of the present invention to provide an improved automatic method for secure analysis of a biological sample to securely and quickly recognize benign or malign changes relative to a healthy sample.

In accordance with a first aspect, the present invention provides a method for the analysis of a biological sample to determine a change relative to a healthy biological sample, with the steps of creating a first image of the biological sample at a first acquisition modality; creating a second image of the biological sample at a second acquisition modality, the first acquisition modality and the second acquisition modality being different, and the first acquisition modality and the second acquisition modality being selected from a group of acquisition modalities including a transmitted-light acquisition modality, a fluorescence acquisition modality, and a phase contrast acquisition modality; classifying the first image on the basis of a first predetermined parameter; classifying the second image on the basis of a second pre-determined parameter, the first image being classified independently of the second image; and depending on the classification results, determining if the biological sample comprises a change relative to a healthy biological sample.

In the preferred embodiment of the present invention, an immunocytometric method is provided, which enables to unambiguously identify tumor cells and to prognosticate the progression of dysplastic cells in tumor cells.

Herein, the present invention is based on the innovative concept in which for the first time morphometric (detected by measurement) cell image information is combined with information about the degree of oxidative DNA damage that is significantly increased in tumor cells and in pre-cancerous cells converting to tumor cells. Morphometric image information is obtained by means of a microscope for transmitted light. The determination of the DNA damage amounts in individual cells takes place in the fluorescent microscope by the measurement of the fluorescent signals that are emitted from antibodies specifically bound to defined DNA damage (8-oxoguanine).

The advantage of the present invention is that a significant increase in image information in comparison with existing methods is combined with new knowledge-based trainable image evaluation methods, and thus a procedural technique so far unequalled with respect to the classification security and the application sensitivity has been developed.

According to a preferred embodiment, the inventive method is applied in the analysis of smears (cervical swabs). As progress for the analysis of this sample, an optimized process for the rendition of these samples is performed, during which mucus is removed, cells are diced on the carrier or slide, highly accurate reproducible preparation and treatment with antibodies is performed. Subsequently, in this embodiment, the capture of high-quality microscopic transmitted-light, color contrast, and fluorescence pictures takes place, which performs an automatic recognition of dysplasia or tumor-suspicious cells and their prognosis in the microscopic imaged pictures by means of a computer-aided image evaluation system.

An advantage of this procedure is that the image information on the slide is not only systematically digitally detected and archived, but the subjective proficiency regarding results of the qualified medical staff is replaced by the objective computer-aided component.

The present invention is not limited to the examination of smears, but is also transferable to the early detection of other kinds of cancer, such as the bladder, mamma, lung, and thyroid carcinoma, as well as malign discharges and the like.

BRIEF DESCRIPTION OF THE DRAWINGS

These and other objects and features of the present invention will become clear from the following description taken in conjunction with the accompanying drawings, in which.

DESCRIPTION OF THE PREFERRED EMBODIMENTS

Figure 1:
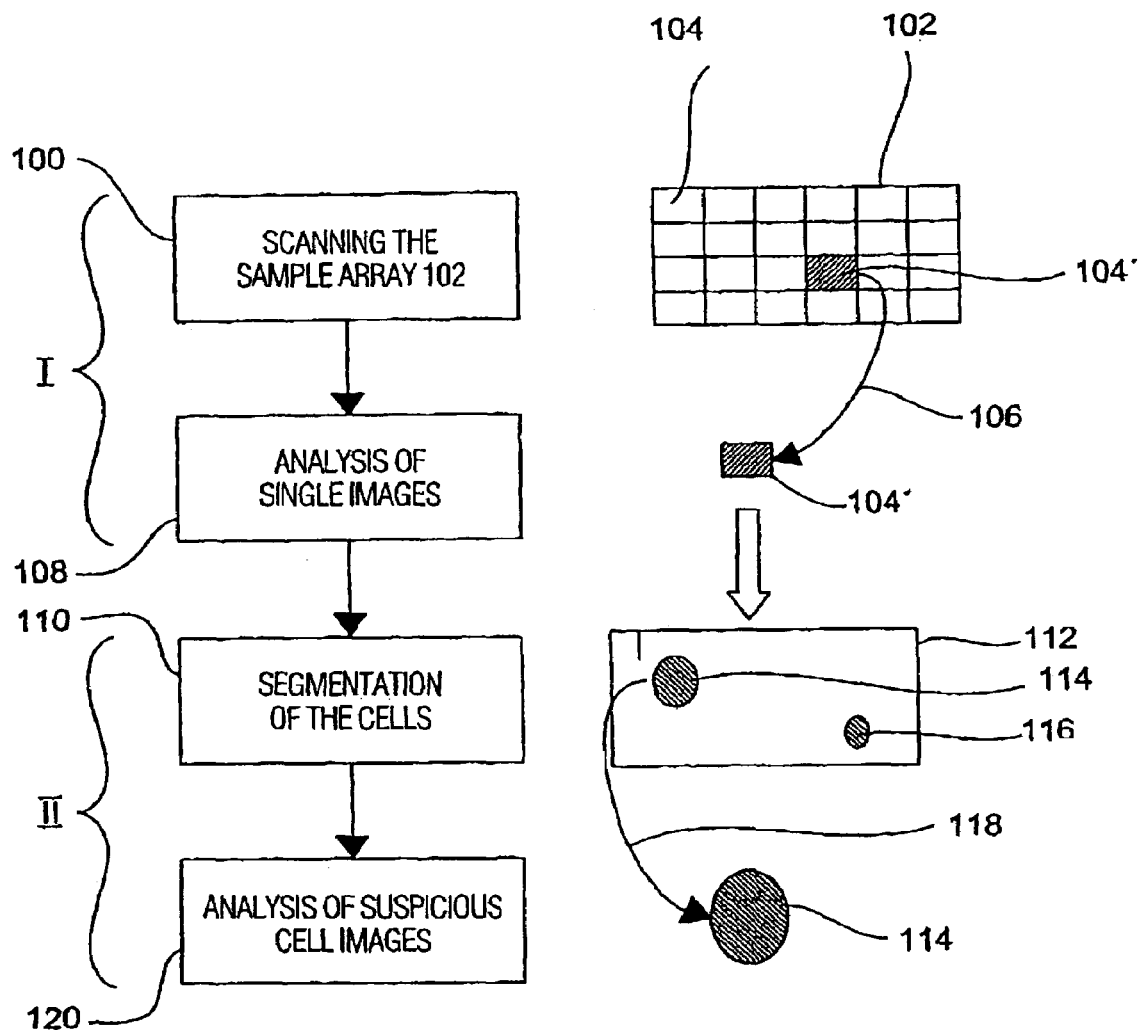
FIG. 1 is a schematic illustration of a first embodiment of the method according to the invention.

Before preferred embodiments of the present invention are subsequently set forth in greater detail, general aspects of the invention are again explained in the following.

One possibility for the recognition of tumor cells is to detect their oxidative DNA damage. The tumor cells always have higher oxidative DNA damage than cells of the corresponding normal tissue. This can be seen from a series of publications on the content of the mutagenic base damage 8-oxaguanine and other oxidative DNA change in tumor and normal tissues of the gastro-intestinal tract and of the lung, prostate, brain, ovaries, mamma, etc., such as in Olinski et al. (1992) FEBS Lett. 309, 193-198; Jaruga et al. (1994) FEBS Lett. 341, 59-64; Musarrat et al. (1996) Eur. J. Cancer 32A, 1209-1214; Malins et al. (1996) Proc. Natl. Acad Sci. USA 93, 2557-2563; Matsui et al (2000) Cancer Lett. 151, 87-95. Even in leukemia cells increased 8-oxoguanine levels have been found (Senturker et al. (1997) FEBS Lett., 416, 286-290). The persistence of this damage leads to the formation of defined mutation patterns in the cellular DNA of the target tissue (e.g. the tumor tissue), which are typical of oxidative DNA damage, as it is described in Moriva (1993) Proc. Natl. Acad. Sci. USA, 90, 1122-1126; Reid et al. (1993) Proc. Natl. Acad. Sci. USA, 90, 3904-3907; Du et al. (1994) Mol. Carcinog., 11, 170-175; Turker et al., (1999) Cancer Res., 59, 1837-1839, for example.

Further examinations have shown increased 8-oxoguanine values not only in tumors, but also in pre-cancerous tissues (Musarrat et al. (1996) Eur. J. Cancer 32A, 1209-1214; Olinski et al. (1995) Free Radic. Boil. Med., 18, 807-813). Thus, oxidative DNA damage already develops in preliminary cancer stages, and it is possibly responsible for the development of cancer cells. Animal experiment examinations have confirmed this assumption. There is indeed a causal connection between the formation and persistence of increased 8-oxoguanine contents and the development of tumors, as this is described in Driscoll et al. (1995) Exp. Lung Res., 21, 941-956; Nehls et al. (1998) Environ. Health Perspect., 105 Suppl. 5, 1291-1296). Apart from this observation, the examinations have provided three further important pieces of information subsequently set forth:

(a) The development of oxidative DNA damage long proceeds the tumor development.

(b) The oxidative damage of the DNA has to persist over a long period of time until cancer develops. For the development of cervical tumors from pre-malign preliminary stages (TIN III), an average of 16 years has been determined for women (Forsmo et al. (1997) Int J. Cancer, 71, 4-8).

(c) The oxidative damage has to take place in the DNA of divisible cells. Only in these cells is the damage transferred to mutations during the DNA replication, and passed on to the daughter cells.

The degree of the oxidative DNA damage may thus be used to
  identify an existing tumor cell, or
  to prognosticate if a dysplasia will develop into a tumor.

Furthermore, sample rendition is required for the inventive method, which uses an immunocytochemical method, according to an embodiment. Immunocytochemical methods are only used in a limited manner in diagnostics so far, for which there are the two following reasons. In contrast to immunohistochemical examinations on paraffin-embedded tissues, it is more difficult to conduct the immunocytochemistry in a standardized manner, and the quality of the immune-stained cytological preparations has strong variations. In addition, after the various incubation steps for immunocytochemical stainings, the morphology of the cells is strongly impeded. According to the present invention, a method is applied in which the quality of immunocytochemical stainings in ensured and their reproduction is standardized so that the morphology of the treated cells remains in better condition and an image evaluation takes place in a reliable manner. By sample rendering or optimized fixing of the cell preparations as early as possible immediately after the take-out as well as a modified Papanicolaou or Pappenheim staining in combination with the immunocytochemistry, it is possible to obtain better and more standardized results. Hereby, an optimized sample rendition and staining of the cells is achieved, whereby both conventional transmitted-light microscopic and automated evaluations can be performed more reliably.

In FIG. 1 a schematic representation of a first embodiment of the method according to the invention is illustrated. The individual procedural steps are shown in the blocks in the left column, and, in parallel to the left column, the corresponding items or elements, on which the individual steps act, are illustrated in the right column.

According to the embodiment illustrated, the inventive method is generally divided into a first sub-step I and a second sub-step II.

In sub-step I, first the sample array 102 is scanned in step 100. The sample array 102 comprises a plurality of single samples 104, with a biological sample 104' being selected from the array 102 due to step 100, as this is shown by means of the arrow 106. After an individual sample 104' has been selected, an analysis of single images referring to the sample 104' takes place in step 108, as it is still further explained in the following.

Starting from the analysis results of the single images, it is determined whether the biological sample 104' is tumor-suspicious, or not. If the tumor suspicion is answered in the affirmative, the method proceeds to the second sub-step II, according to the embodiment illustrated in FIG. 1, in which first the single images are segmented in step 110 so that sub-images with individual cells develop, as it is exemplarily shown in FIG. 1 at 112, showing a sub-image with two individual cells 114 and 116. As it is illustrated by means of the arrow 118, the cell, in the example shown, the cell 114, is selected, and an analysis of this suspicious cell 114 takes place in step 120. Depending on the analysis result, it may be asserted whether the tumor-suspicious cell is indeed an already existing tumor cell or is a benign or malign dysplasia.

According to the method according to the invention, mathematical feature operators are iteratively determined from pre-classified reference data sets to classify the detected images of the biological samples. A separation of samples with each a dominant type of feature enables the determination of an accompanying set of operators. If operators orthogonal to each other can be unambiguously associated with the feature types of interest, their discrimination within an image data set may be realized.

In the approaches known so far for the automatic cytology and cytometry, the operators used for the extraction of structure and shape features have been determined on the trial-and-error principle. This procedure has its utmost limit where very complex and specific patterns have to be recognized within varying contexts. With this, the problem is that trying a multiplicity of operators on a reference random sample for determining the relevance with respect to the recognition target leads to computing times of several years due to the enormous size of the search space. Because in the cell analysis the pattern recognition tasks are extremely complex and also very variant in their form, a new approach is required here, as is it taught according to the present invention. Under the boundary conditions of limitedly available computing power and practicable computing time, from an existing operator library those operators are selected that contribute to an optimum classification result.

According to the embodiment described on the basis of FIG. 1, the selection is made in sub-step I and in sub-step II.

In sub-step I, the selection of the operators is globally applied on the level of an image 104', wherein by such an image 104' a unit may be understood that a cytologist sees as whole—maybe at different magnifications—through the eye-piece of his microscope. From a normal cytological sample, depending on the magnification factor, between 12 and 500 of such images may be stored. The automatic parameter selection may be performed independently of each other on single images of different modality, such as transmitted light, phase contrast, and fluorescence, as well as on different cell types (cervix, bladder, lung, etc.). In a sufficiently securely pre-classified image random sample, a good selection result results.

In sub-step II—at the presence of suspicious cells—the object segmenting and the sub-analysis on the single cell level with maximum resolution follows. Here, cell dimension, shape, and structural features are detected, wherein also here the approach of the texture parameter selection is employed. Furthermore, morphometric parameters are determined.

According to the invention, long-term experience of cytologists and cytology assistants in the examination and evaluation of microscopic histological results is coupled with a more objective approach for automatic parameter selection when selecting the cell image and cell parameters to be used for the classification of a cell. Since a complete, optimal search for the selection of ideal parameters would require a computing time of several years, the existing expert knowledge is syntactically and semantically integrated into the automatic selection—coupled to a weighting function.

Hereby, the following advantages are realized:

The parameter selection is performed in several learning phases on the basis of a large pre-classified random sample. Variations for optimizing may be newly trained and stored in configuration files.

By the establishment of several configuration data sets, different cytological preparations (cervix, bladder, lung, . . . ) can be examined with a classification system, and the required algorithms can be adapted. Thereby, such classification systems are no longer limited to one application, and enable dealing with a majority of cytological and histological testing tasks.

In FIG. 2, a more detailed representation of the embodiment of the present invention described on the basis of FIG. 1 is illustrated. From sample array 102 with the multiplicity of single samples 104, a single sample 104' is selected for analysis.

Regarding this single sample 104', three sub-images are created, as it is indicated by the blocks DL, PK and FL. The first sub-image is created by means of a first acquisition modality, namely the microscopic transmitted-light acquisition modality (DL). The second sub-image is obtained by means of the acquisition modality phase contrast (PK), and the third sub-image is obtained by means of the acquisition modality fluorescence (FL). Each obtained sub-image DL, PK, FL is classified separately from each other by means of a selected parameter set, as it is indicated by the blocks $K_1$, $K_2$, and $K_3$. From the classification of the individual sub-images, corresponding classification results result for each sub-image, as it is indicated by the blocks $E_1$, $E_2$, and $E_3$. In step 122, it is determined on the basis of the results $E_1$, $E_2$, and $E_3$ if a change in the sample 104' is present relative to a healthy sample. If this is answered in the negative, the method terminates in step 124, according to the illustrated embodiment. If a change in the sample, e.g. a tumor suspicion, is answered in the affirmative, the method proceeds to step 126 in FIG. 2B. In step 126, the segmenting of the sample 104' already described above takes place, such that the sample is divided into individual areas substantially including a cell or only individual cells, as it is schematically shown in FIG. 2B at 128, 130, and 132.

Figure 2A:
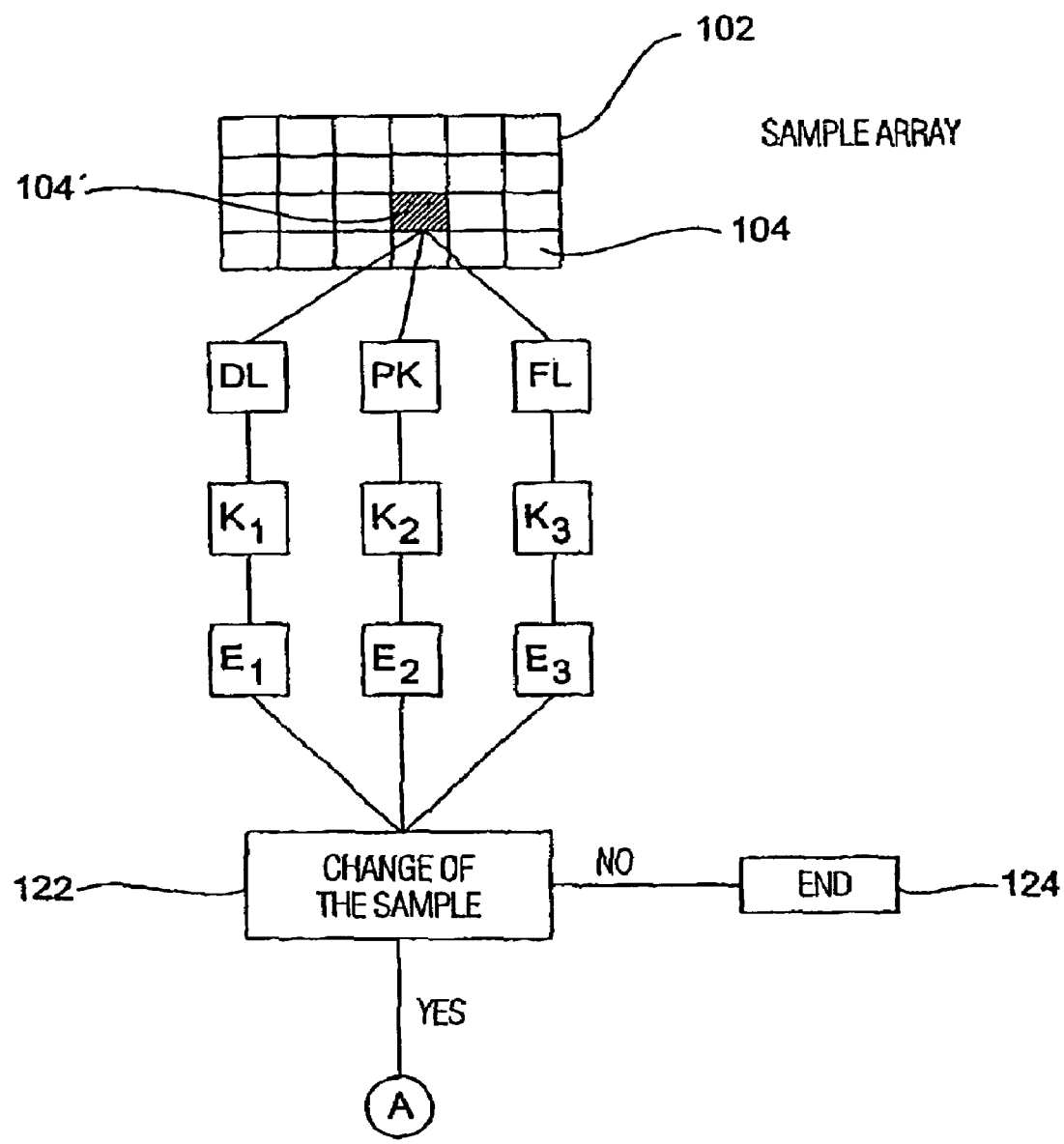
FIGS. 2A and B are more detailed illustrations of the individual steps of the embodiments described on the basis of FIG. 1.
Figure 2B:
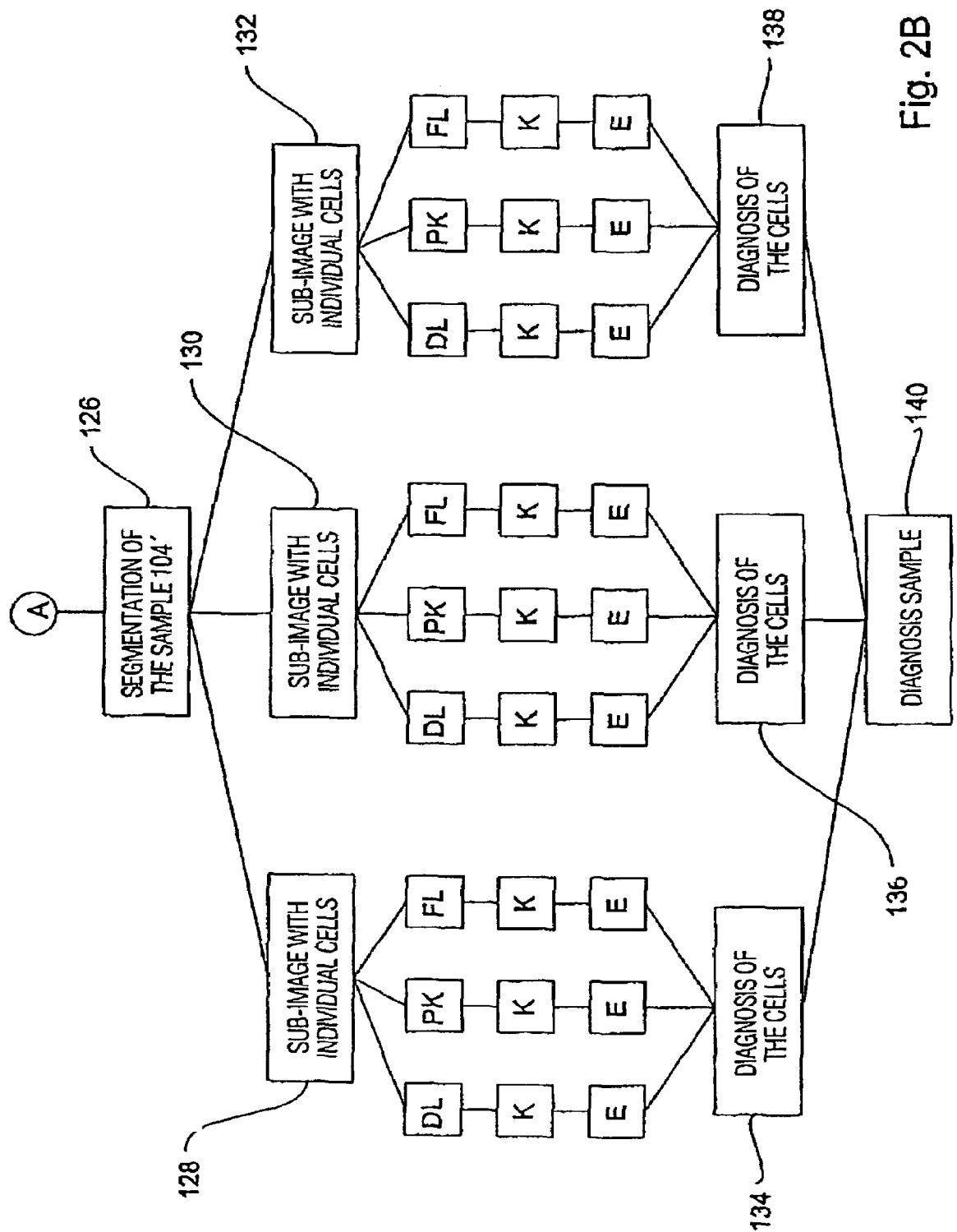

For each of the portions 128 to 132 or for each sub-image with individual cells, in turn sub-images in the three acquisition modalities already described above, transmitted light, phase contrast, fluorescence (DL, PK, FL), are created, as it is illustrated by the corresponding blocks in FIG. 2B. Then classification of the individual sub-images takes place, as it is illustrated by the blocks K in FIG. 2B. As described above, here the classification of the individual sub-images also takes place in different acquisition modalities independently of each other, to achieve corresponding classification results (see blocks E).

On the basis of the classification results of the individual portions or sub-images, corresponding diagnoses of the cell or the cells 134, 136, 138 are achieved, which are used for the diagnosis of the entire biological sample in step 140.

The more detailed embodiment described on the basis of FIG. 2 first includes the pre-classification on the image level, as it is shown in FIG. 2A. For each of the samples 104 under examination three single images are created that are obtained by means of the acquisition modalities transmitted light (DL), phase contrast (PK), and fluorescence (FL). First these three images are classified separately from each other on the image level, i.e. each as a whole. Here, an extended and modified automatic texture analysis method is used whose extension is that a supplement is integrated by texture methods, which is especially necessary for cytological preparations. Furthermore, an integration of present expert knowledge is given. According to the invention, automatic selection of the parameters necessary and sufficient for these classification tasks is done from a store of about 600 to 1,000 texture parameters (color, statistical, texture, shape parameters). The required parameters are determined due to a representative image random sample by intelligent selection, wherein, among other things, the quality, the meaningfulness, and the sharpness of separation of the selected parameters are important in the classification. For each acquisition modality (DL, PK, and FL) a parameter set of its own is determined each independently of each other for the classification.

Subsequently, in step 122, the correlation of the pre-classification results from several acquisition modalities takes place. The independent classification results $K_1$, $K_2$, $K_3$ of the three acquisition modalities are correlated with each other to make a decision whether the biological sample 104' is to be rated healthy or tumor-suspicious. By a correspondingly suitable choice of the decision boundary, about 75% of the samples are culled as not tumor-suspicious with high security also by this kind of pre-classification. All samples rated tumor-suspicious are subjected to a further classification stage on cell level in the subsequent steps shown in FIG. 2B.

In FIG. 2B, in step 126, first the cell segmentation is conducted. In order to examine all tumor-suspicious image samples in greater detail and supply them to the fine classification, first the individual cells are segmented from these image samples. The segmentation of the cells again takes place on all three image extracts DL, PK, and FL separately from each other. The result of this segmentation forms, as smallest unit, image sectors with—in the ideal case—an individual cell each. By suitable preparation of the samples in the run-up, it is ensured that only few cell conglomerates, i.e. cell overlaps, are to be seen.

Subsequently, the segmented cells are classified. First each individual cell is classified separately, with the above-described method for automatic knowledge-based parameter selection also being used here. On the cell level, not only color, texture and statistical parameters are used, but furthermore also shape parameters of the segmented cell are considered. Here, by means of intelligent selection from a store of 600 to 1,000 descriptive cell parameters, also those are selected with which the cell types appearing in the different acquisition modalities can be discriminated from each other with high security.

Subsequently, the fusion of the classification results and a decision take place. The cell level classification is at first conducted separately for each image modality, and then both the segmented cells of the three views have to be registered with each other and the classification results have to be processed, to reach a differentiated diagnosis.

In the embodiment described above, the sub-images at the different acquisition modalities may be obtained for the segmented cells either due to the sub-images already created in the first main step by simple segmentation thereof, or a corresponding segmentation of the sample and renewed creation of the images in the second portion is conducted.

Furthermore, it should be understood that the method according to the invention is not limited to the preferred embodiment. The method according to the invention rather enables an analysis of biological samples to determine if these have changes relative to healthy tissue. Starting from this classification of a sample, various possibilities of further analysis are possible, provided that this is desired at all. For some applications it may be sufficient to determine that changes in the sample have taken place relative to healthy tissue or healthy samples.

In again other applications, e.g. semi-automated analysis methods, the cytologist may be supplied from an entire sample with only those single samples for further inspection which have a corresponding suspicious change in the material, and the cytologist will then perform final assessment.

The third possibility is the complete automation, as it has been described above on the basis of the figures.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. A method for the analysis of a biological sample to determine a change relative to a healthy biological sample, comprising:
   creating a first image of the biological sample at a first acquisition modality;
   creating a second image of the biological sample at a second acquisition modality, the first acquisition modality and the second acquisition modality being different, and the first acquisition modality and the second acquisition modality being selected from a group of acquisition modalities including a transmitted-light acquisition modality, a fluorescence acquisition modality, and a phase contrast acquisition modality;
   classifying the first image on the basis of a first predetermined parameter;
   classifying the second image on the basis of a second predetermined parameter, the first image being classified independently of the second image; and
   depending on the classification results, determining if the biological sample comprises a change relative to a healthy biological sample.

2. The method of claim 1, comprising:
   creating a third image of the biological sample at a third acquisition modality; and
   classifying the third image on the basis of a third predetermined parameter, the third image being classified independently of the first image and the second image.

3. The method of claim 1, comprising the following steps in the determination of a change of the biological sample, in order to determine whether the change of the biological sample is benign or malign:
   setting at least one portion of the biological sample, the portion substantially comprising one element or substantially individual elements;
   creating a first sub-image of the portion of the biological sample at a fourth acquisition modality;
   creating a second sub-image of the portion of the biological sample at a fifth acquisition modality;
   classifying the first sub-image on the basis of a fourth predetermined parameter;
   classifying the second sub-image on the basis of a fifth predetermined parameter, the first sub-image being classified independently of the second sub-image; and
   depending on the classification results, determining whether the change of the biological sample is benign or malign.

4. The method of claim 3, comprising:
   creating a third sub-image of the portion of the biological sample with a sixth acquisition modality; and
   classifying the third sub-image on the basis of a sixth predetermined parameter, the third sub-image being classified independently of the first sub-image and the second sub-image.

5. The method of claim 3, wherein the biological sample includes a plurality of cells, with the first sub-image, the second sub-image, and the third sub-image substantially including a cell or substantially individual cells.

6. The method of claim 1, wherein the first acquisition modality, the second acquisition modality, the third acquisition modality, the fourth acquisition modality, the fifth acquisition modality, and the sixth acquisition modality are selected from a group including transmitted light, phase contract, and fluorescence, and wherein the first pre-determined parameter, the second pre-determined parameter, the third pre-determined parameter, the fourth pre-determined parameter, the fifth pre-determined parameter, and the sixth pre-determined parameter are selected from a group including cell dimension, shape, structure, color, texture, and statistical features, morphometric data, and data of the oxidative damage of cells.

7. The method of claim 6, wherein the first acquisition modality and the fourth acquisition modality are the transmitted light acquisition modality, the second acquisition modality and the fifth acquisition modality are the phase contrast acquisition modality, and the third acquisition modality and the sixth acquisition modality are the fluorescent acquisition modality, wherein for each acquisition modality a parameter set each is determined independently of each other from the group of predetermined parameters for classification.

* * * * *